United States Patent
Domnich et al.

(10) Patent No.: US 11,969,230 B2
(45) Date of Patent: Apr. 30, 2024

(54) PASSIVE TRANSPONDER SYSTEM AND PRESSURE WAVE MEASURING DEVICE

(71) Applicant: VesselSens GmbH, Bonn (DE)

(72) Inventors: Alexej Domnich, Bonn (DE); Fabian Tutsch, Cologne (DE)

(73) Assignee: VesselSens GmbH, Bonn (DE)

( * ) Notice: Subject to any disclaimer, the term of this patent is extended or adjusted under 35 U.S.C. 154(b) by 768 days.

(21) Appl. No.: 16/956,567

(22) PCT Filed: Dec. 18, 2018

(86) PCT No.: PCT/EP2018/085523
§ 371 (c)(1),
(2) Date: Jun. 20, 2020

(87) PCT Pub. No.: WO2019/121700
PCT Pub. Date: Jun. 27, 2019

(65) Prior Publication Data
US 2021/0022610 A1    Jan. 28, 2021

(30) Foreign Application Priority Data

Dec. 22, 2017    (DE) ...................... 10 2017 223 695.7

(51) Int. Cl.
*A61B 5/00*    (2006.01)
*A61B 5/0215*    (2006.01)
*A61B 5/0265*    (2006.01)

(52) U.S. Cl.
CPC .......... *A61B 5/0031* (2013.01); *A61B 5/0215* (2013.01); *A61B 5/6862* (2013.01); *A61B 5/0265* (2013.01); *A61B 2562/0247* (2013.01)

(58) Field of Classification Search
CPC ................ A61B 5/0031; A61B 5/6862; A61B 2562/0247; A61F 2/86
See application file for complete search history.

(56) References Cited

U.S. PATENT DOCUMENTS 6,939,299 B1*   9/2005 Petersen .................. A61B 3/16
                                                               600/587
2005/0080346 A1   4/2005 Gianchandani et al.
(Continued)

FOREIGN PATENT DOCUMENTS

WO    WO 02/098296 A1    12/2002
WO    WO 2006/096685 A1    9/2006
(Continued)

OTHER PUBLICATIONS

Domnich, "Determination of the Restenosis Degree Inside the Implanted Stent with Integrated Wireless Pulse Wave Velocity Sensor," *Fraunhofer Institute for Manufacturing Engineering and Automation IPA* (Oct. 9, 2014) 15 pgs.
(Continued)

*Primary Examiner* — Charles A Marmor, II
*Assistant Examiner* — Raymond P Dulman
(74) *Attorney, Agent, or Firm* — Leydig, Voit & Mayer, Ltd.

(57) ABSTRACT

The invention relates to a passive transponder system comprising a first or second conductor loop structure and a first and a second capacitive pressure sensor, wherein each conductor loop structure is coupled to one of said capacitive pressure sensors to form a resonant circuit, and the first conductor loop structure is positioned at a non-vanishing angle in relation to the second conductor loop structure. The resonant frequencies of the resonant circuits are selected such that they do not overlap to result in beating. The invention also relates to a pressure wave measuring device comprising such a passive transponder system, and a readout unit.

17 Claims, 9 Drawing Sheets

(56) References Cited

U.S. PATENT DOCUMENTS

| | | | | |
|---|---|---|---|---|
| 2006/0047205 A1* | 3/2006 | Ludomirsky | ........ | A61B 5/0215 600/486 |
| 2010/0262036 A1* | 10/2010 | Najafi | .................... | A61B 5/031 600/561 |
| 2011/0115497 A1* | 5/2011 | Cros | .................... | A61B 5/0031 324/633 |
| 2012/0059445 A1* | 3/2012 | Stevenson | ................ | A61N 1/05 607/116 |
| 2012/0086538 A1* | 4/2012 | Chu | .................... | H01F 17/0013 336/206 |
| 2013/0296722 A1* | 11/2013 | Warnking | ............ | A61B 5/6851 600/488 |
| 2020/0367769 A1 | 11/2020 | Domnich et al. | | |

FOREIGN PATENT DOCUMENTS

| | | | | |
|---|---|---|---|---|
| WO | WO 2007/078770 A1 | 7/2007 | | |
| WO | WO-2010088279 A2 * | 8/2010 | ........... | A61B 5/0031 |
| WO | WO 2012/100959 A1 | 8/2012 | | |
| WO | WO-2012100959 A1 * | 8/2012 | ........... | A61B 5/0031 |

OTHER PUBLICATIONS

Schächtele, "A Bifrequent Passive Sensor System for Measurement of The Pulse Wave Velocity in a Stent," *IEEE Engineering in Medicine and Biology Society* (EMBC Annual International Conference) Orlando, FL (Aug. 2016) pp. 1926-1929.

Zurich Instruments, "Principles of lock-in detection and the state of the art," (2016) 10 pgs. Retrieved from the Internet: https://www.zhinst.com/sites/default/files/li_primer_zi_whitepaper_principles_of_lock-in_detection.pdf.

European Patent Office, International Search Report in International Application No. PCT/EP2018/085523 (dated May 27, 2019).

European Patent Office, Written Opinion in International Application No. PCT/EP2018/085523 (dated May 27, 2019).

International Bureau of Wipo, International Preliminary Report on Patentability in International Application No. PCT/EP2018/085523 (dated Jun. 23, 2020).

U.S. Appl. No. 16/969,166, filed Aug. 11, 2020.
U.S. Appl. No. 17/041,328, filed Sep. 24, 2020.
U.S. Appl. No. 17/041,939, filed Sep. 25, 2020.

* cited by examiner

FIG 6 Variant 2 Embodiment 2 Side View

FIG 7 Variant 2 Embodiment 2 Isometric View

FIG 8  Variant 2 Embodiment 2 Detail View

Turn diameter 6mm

FIG 9  Variant 2 Embodiment 2 View Through

PASSIVE TRANSPONDER SYSTEM AND PRESSURE WAVE MEASURING DEVICE

CROSS-REFERENCE TO RELATED APPLICATIONS

This patent application is the U.S. national phase of International Application No. PCT/EP2018/085523, filed on Dec. 18, 2018, which claims the benefit of German Patent Application No. 10 2017 223 695.7, filed Dec. 22, 2017, the disclosures of which are incorporated herein by reference in their entireties for all purposes.

The invention relates to a passive transponder system comprising a first or second conductor loop structure and a first and a second capacitive pressure sensor, wherein in each case a conductor loop structure is coupled to one of the capacitive pressure sensors to form a resonant circuit, wherein the first conductor loop structure is at a non-vanishing angle to the second conductor loop structure. The resonant frequencies of the resonant circuits are selected such that they do not superpose one another in such a way as to produce a beat. The invention also relates to a pressure wave measuring device comprising such a passive transponder system and also a reader unit.

Devices which use inductively coupled communication between a transponder or a passive resonant circuit and a reader are used for various applications. The transponder or the passive resonant circuit is supplied with energy via inductive coupling. At the same time, signals and thus information are also transmitted via such a coupling.

Such devices are used for example in medicine in order to obtain information about the blood flow in vessels. In this case, the transponder may be designed as a coil which encircles the blood vessel in question.

It is problematic that such coils have a pronounced figure-of-eight-shaped directional characteristic. As a result, the coupling between the reader coil and the transponder coil is substantially dependent on the orientation of the transponder coil relative to the reader coil. A maximum signal can be achieved when the field generated by the reader coil passes through the transponder coil to the maximum extent. If, on the other hand, the field of the reader coil does not pass through the sensor coil at all, for example when said coils are at an angle of 90° to one another, no coupling is achieved and reading becomes impossible.

One possible embodiment of the transponder coil is a saddle-shaped winding in which the conductor tracks of the coil follow a cylindrical surface and the coil axis is perpendicular to the cylinder axis of this cylindrical surface.

When the transponder coil is implanted, it is impossible or very difficult to determine how such a saddle-shaped coil is oriented around the blood vessel in question. If the axis of the saddle-shaped coil is parallel to the axis of the reader coil, then the coupling is at a maximum. If the coil axes are perpendicular to one another, no coupling is achieved at all.

One object of the present invention is to specify a passive transponder which enables good coupling to a reader coil in a reliable and controllable manner. A further object is to specify a pressure wave measuring device in which good and controllable reading of the signal is possible.

This object is achieved by the features of the passive transponder system, the pressure wave measuring device, and the method for producing a passive transponder system described herein and the advantageous developments thereof.

According to the invention, a passive transponder system is specified which comprises a first conductor loop structure having at least one turn and a second conductor loop structure having at least one turn. A conductor loop structure can be understood here to mean a structure which is created from an electrical conductor and which comprises at least one turn of the conductor. The conductor is in this case preferably of elongate shape itself, for example in the form of a wire or conductor track, and is shaped along its longitudinal direction to form the at least one turn.

The passive transponder system additionally comprises a first capacitive pressure sensor and a second capacitive pressure sensor. A capacitive pressure sensor will be understood here to mean a capacitance, that is to say a capacitor, the value of which is dependent on a pressure applied to the sensor. In a simple example, such a capacitive pressure sensor may be designed as a closed volume, on the opposing surfaces of which a capacitor plate is arranged in each case. When a pressure is applied to such a structure, the distance between the capacitor plates changes and thus the capacitance of the capacitor formed by the capacitor plates changes. The capacitance can therefore be used as a measure of the pressure applied.

According to the invention, the first capacitive pressure sensor is coupled to the first conductor loop structure to form a first resonant circuit. This first resonant circuit has a resonant frequency which will hereinafter be referred to as the "first resonant frequency". In addition, the second capacitive pressure sensor is electrically coupled to the second conductor loop structure to form a second resonant circuit, the resonant frequency of which will be referred to as the "second resonant frequency".

The turns of the conductor loop structures are each wound around at least one turn axis. Therefore, the at least one turn of the first conductor loop structure is wound and at least one first turn axis and the at least one turn of the second conductor loop structure is wound around at least one second turn axis. Here, a turn axis will be understood to mean a straight line which is perpendicular to a surface in which the turn in question runs. Preferably, the turn axis should be perpendicular at a centre point of the area of this surface that is encircled by the turn in question. The centre point can be regarded here as being that point relative to which the turn in question is point-symmetrical. The fact that the turn is point-symmetrical is optional here. The point-symmetry preferably exists in projection onto a plane to which the turn axis is perpendicular. The turn axis passes through this plane preferably at a centre point of the projection of the turn onto this plane. A helical turn, that is to say a turn which has a somewhat larger or smaller radius after running around the turn axis than at its opposite end, should likewise be regarded here as point-symmetrical in this sense.

According to the invention, the at least one first turn axis and the at least one second turn axis are at a non-vanishing angle to one another. The angle is therefore greater than zero and less than 180°. The angle should not be 0° and should not be 180°. Preferably, the angle is 90°. According to the invention, the turn axes must not intersect. In this case, the angle between projections of the turn axes in a direction perpendicular to one or both of the turn axes will be measured on a common plane.

The passive transponder system of the invention can also be referred to as a passive transponder. The first resonant circuit and the second resonant circuit may advantageously be structurally connected to one another. However, it is also possible to embody the two resonant circuits in a manner not structurally connected to one another.

As is known, the resonant frequency of a resonant circuit can be set by choosing the capacitance and inductance of the conductor loop structure. Preferably, the first resonant frequency and the second resonant frequency differ at least to such an extent that they do not superpose one another in such a way as to produce a beat. The first resonant frequency and the second resonant frequency are therefore preferably selected such that, when they are superposed, they do not form a beat. The signals generated by the individual resonant circuits can be separated particularly easily as a result.

It has proven to be advantageous if the resonant frequency of the first and second resonant circuit differ by at least twice the bandwidth of the first or second resonant circuit. Advantageously, the resonant frequencies of the first and second resonant circuit differ at least by twice the bandwidth of that one of said two resonant circuits that has the greater bandwidth. Advantageously, the bandwidth here is the so-called 3 dB bandwidth, which is the difference of the upper −3 dB cutoff frequency $f_2$ and the lower −3 dB cutoff frequency $f_1$. The cutoff frequencies are those frequencies at which the resonance curve intersects the value −3 dB in each case. The bandwidth B can also be defined as $B=f_2-f_1=f_0/Q$, where $f_0=\sqrt{(f_1 f_2)}$ and Q is the quality of the resonant circuit. For conventional sensor resonant circuits, the minimum gap could therefore be 2 MHZ for example.

In one advantageous embodiment, the first and the second conductor loop structure may be designed as flat coils which are arranged on surfaces of a carrier structure. If the conductor loop structures in this case have more than one turn, these turns may each run on a common surface, wherein adjacent turns in each case have a somewhat larger diameter so that adjacent turns encircle one another. In this way, it is possible to produce coils which are flat and have any desired number of turns. In this embodiment, the surface of the flat coils, that is to say the surface in which the turns run, may be the surface of the carrier structure.

With particular advantage, the first conductor loop structure may be arranged on an inner surface of the carrier structure and the second conductor loop structure may be arranged on an outer surface. However, it is also possible that both conductor loop structures are arranged on the same surface of the carrier structure, wherein then the conductor loop structures are advantageously insulated from one another. To this end, the conductor tracks of the conductor loop structures may for example be sheathed with an insulator. It is also possible first to apply one of the conductor loop structures and then to coat this entire surface of the carrier structure with an insulating material and then to apply the other conductor loop structure. In this way, any number of conductor loop structures can be arranged on the same surface of the carrier structure. However, it is also possible that the conductor track of one of the conductor loop structures extends to the other surface of the carrier structure only at the point where it crosses a conductor track of the other conductor loop structure.

Advantageously, the carrier structure may be shaped as part of a cylinder, as a cylinder, as part of a hose, as a hose, as part of a tube or as a tube. A cylinder may be understood here to mean a surface which at all points is at the same distance from a common line. This line will be referred to here as the cylinder axis. The line may be curved or may be a straight line. Preferably, the surface is closed around said line. With particular preference, a base area of the cylinder is circular, but other shapes of the base area are also possible. A cylinder having a circular base area can also be referred to as a hose or as a tube, wherein in the case of a hose said line may be curved, and wherein in the case of a tube said line may be a straight line. Shaped as part of a cylinder may be understood here to mean a shape for which all points are part of a cylinder surface but without forming a complete cylinder surface. Correspondingly, part of a hose or part of a tube can be understood to mean a surface for which all points are part of a hose or tube but without entirely completing the latter. The carrier structure may then have for example the shape of a hose or tube which is three-quarters closed. For use in blood vessels, preference is given to the hose shape and tube shape since these match the geometry of the blood vessel.

In this embodiment, the angle between the turn axes of the first and second conductor loop structure can be freely selected within the scope of what is predefined by the invention. If the conductor loop structures are arranged on surfaces of a tube-shaped or hose-shaped structure, they may be designed in a saddle-shaped manner. With particular advantage, they may be designed in such a way that the conductor loops or turns each have two straight sections, in which they run parallel to a cylinder axis of the carrier structure, wherein the straight sections are in each case connected to one another by curved sections, in which the turn in question runs in a curved manner around the cylinder axis of the carrier structure. The pressure sensors may in this case likewise be arranged on the surfaces of the carrier structure, the first capacitive pressure sensor preferably being arranged on that surface of the carrier structure on which the first conductor loop structure is also arranged, and the second capacitive pressure sensor preferably being arranged on that surface of the carrier structure on which the second conductor loop structure is also arranged.

The curved sections of the turns preferably have a length of 180°, which is equivalent to saying that the respective two straight sections of the turns are located precisely opposite one another in relation to the cylinder axis. As a result, the area encircled by the turn is at a maximum and thus the coupling is maximized.

With particular advantage, a plastic tube or a plastic hose is suitable as the carrier structure. The two conductor loop structures are then electrically insulated from one another by the plastic tube or the plastic hose. The carrier structure may for example be made of polyimide.

Preferably, the coil axes are perpendicular to one another in the sense described above, as a result of which the mutual influencing is minimized and a directional characteristic that is best matched to the circular shape is achieved. During use, the cylinder axis of the carrier structure may be coaxial to the longitudinal axis of a blood vessel on which the carrier structure is arranged. Since, due to anatomy, the blood vessels in the human body largely run parallel to the longest dimension of the body, the aforementioned directional characteristic will preferably be approximately in a plane of the circular shape, which is perpendicular to the cylinder axis or longitudinal axis of the carrier structure. The directional dependence is particularly advantageous in this radial direction because a correction by displacing the reader coil around the vessel would be possible without signal losses only when the vessel is located exactly in the middle of the cylindrical body part, which is de facto the case only in a few exceptional cases. In all other cases, the vessel will be located closer to the surface of the body part in one direction and the coupling to the transponder coil should also be as good as possible precisely at this location. Although axial displacement of the reader coil relative to the sensor coil is possible, a correction can nevertheless be made simply by displacing the reader coil along the body part.

The aforementioned flat coil may advantageously have a round, oval, square or rectangular periphery, with the shapes in question being curved in each case with the corresponding surface of the carrier structure. Preferably, the central width of the coil in the unbent state, that is to say in the flat state, is equal to three-quarters of the circumference of the carrier structure.

In one advantageous embodiment of the invention, the first conductor loop structure may have a plurality of groups of turns arranged next to one another in the direction of a main axis. Each group comprises at least one turn. Therefore, even one individual turn can be understood as a group in this sense. Each of the groups of turns of the first conductor loop structure can be wound around a separate first turn axis, wherein preferably the first turn axes of the different groups are parallel to one another and are spaced apart from one another by a non-vanishing distance. Preferably, these distances are the same for all respectively adjacent groups of turns of the first loop structures. Turns of the same group of turns may therefore be wound around the same turn axis. The turn axes of different groups may be different, that is to say non-coaxial, and may be spaced apart from one another.

Correspondingly, the second conductor loop structure may advantageously have a plurality of groups of turns arranged next to one another in the direction of the main axis. Each group comprises at least one turn. Therefore, even one individual turn can be understood as a group in this sense. It is then once again advantageous to wind each of the groups of turns of the second conductor loop structure around separate second turn axes, wherein the second turn axes are preferably parallel to one another and are spaced apart from one another by a non-vanishing distance. Here, too, these distances are preferably the same for all the respectively adjacent second turn axes. Turns of the same group of turns may therefore once again be wound around the same turn axis. The turn axes of different groups may be different, that is to say non-coaxial, and may be spaced apart from one another.

The fact that turns are arranged next to one another means firstly that the turn axes are arranged next to one another. Turns of adjacent groups of the same conductor loop structure, which are arranged next to one another, may overlap one another, may be directly contiguous or may be spaced apart from one another.

If each group comprises only one turn, the first conductor loop structure may have a plurality of turns arranged next to one another in the direction of a main axis, wherein each of the turns of the first conductor loop structure is wound around a separate turn axis, wherein the first turn axes are spaced apart from one another by a non-vanishing distance.

Correspondingly, the second conductor loop structure may have a plurality of turns arranged next to one another in the direction of the main axis, wherein each of the turns of the second conductor loop structure is wound around a separate second turn axis, wherein the second turn axes are at a non-vanishing distance from one another.

Preferably, the turn axes of adjacent turns or groups of turns of the same conductor loop structure are parallel to one another.

In addition, the distances by which the second turn axes are spaced apart from one another are particularly preferably equal to those distances by which the first turn axes are spaced apart from one another. By virtue of this embodiment, a directional characteristic which best approximates the circular shape can be achieved in a plane perpendicular to the direction in which the turn axes are arranged next to one another. Furthermore, a homogeneous directional characteristic can be achieved over the entire length in the direction in which the turn axes are arranged next to one another. Such a conductor loop structure may be considerably longer than the diameter.

In this embodiment of the invention, the first and the second conductor loop structure may each be produced by means of a wire. With particular advantage, a wire which forms the first conductor loop structure may be passed through turns of that wire which forms the second conductor loop structure. In this way, the first and the second conductor loop structure are advantageously interwoven and can thus form a stable structure. This can be used for example as a stent for a blood vessel. Correspondingly, the wire forming the second conductor loop structure may also be passed through the turns of the first conductor loop structure.

In one advantageous embodiment of the invention, the turns of the first conductor loop structure may extend in two surfaces located opposite one another in relation to the main axis, wherein advantageously the first turn axes are each perpendicular to these opposing surfaces. Advantageously, the turns of the second conductor loop structure may also extend in two surfaces located opposite one another in relation to the main axis, the second turn axes then each being perpendicular to said opposing surfaces. The fact that the two surfaces are located opposite one another in relation to the main axis means here that these surfaces are both perpendicular to a straight line which intersects the main axis, the main axis being arranged between these two opposing surfaces. This embodiment can advantageously be used both in the above-described saddle-shaped embodiment of the conductor loop structures and also in the embodiment with turns arranged next to one another.

If the first and the second conductor loop structure have a plurality of turns arranged next to one another in the direction of the main axis, these turns can accordingly extend in two surfaces located opposite one another in relation to the main axis. With particular advantage, the turns of the first conductor loop structure can in each case run through the turns of the second conductor loop structure, so that the first and the second conductor loop structure are interwoven. Then, along the circumference, in each case a turn of the first conductor loop structure can run through a turn of the second conductor loop structure, wherein this turn of the second conductor loop structure runs, on its side remote from said first turn, through a turn of the first conductor loop structure. This last-mentioned turn of the first conductor loop structure can run on that surface which is located opposite the surface in which the first-mentioned turn of the first conductor loop structure runs. The last-mentioned turn of the first conductor loop structure can then mesh with a further turn of the second conductor loop structure, which in turns meshes with the first-mentioned turn of the first conductor loop structure. In this way, a weave which completely surrounds the main axis can be formed by the turns of the first and second conductor loop structure, in which the turns of the first conductor loop structure are located opposite one another and the turns of the second conductor loop structure are located opposite one another. The turns of the first conductor loop structure and of the second conductor loop structure mesh with one another in each case. In one advantageous embodiment of the invention, the first turn axes of the first conductor loop structure are located between the second turn axes of the second conductor loop structure in a direction along the main axis. As a result, a magnetic field generated by the turns of the first conductor loop structure passes through the turns of the second conductor loop structure as little as possible and a magnetic field generated by the turns of the second conductor loop structure passes through the turns of the first conductor loop structure as little as possible. This improves the directional characteristic in the radial direction.

In order that the first and second conductor loop structures can be interwoven as described above, it is advantageous if the wire from which the first and the second conductor loop structure are formed are sheathed with electrical insulation. By way of example, use can be made of DFT wire, which has a core made of Au or Ag and is sheathed with NiTi.

In terms of the electrical and electromagnetic behaviour, the described interweaving of the first and second conductor loop structure corresponds to two or even more coils rotated relative to one another at the desired angle. By virtue of the interweaving, the coil has regions which represent the actual coils and also points of intersection at which these coils can be mechanically brought together and fixed to one another to form a cylindrical overall structure. Such an embodiment can act simultaneously as a coil and as a vessel support, for example as a stent. It can be made of a material which may have both electrical and mechanical and biocompatible properties. Since the coil axes are at a non-vanishing angle to one another, the described good coupling can be achieved regardless of the angle.

In one advantageous embodiment of the invention, the capacitive pressure sensors may be located with their pressure-measuring surface in one of those surfaces in which the conductor loop structure of the corresponding resonant circuit extends. Therefore, the first capacitive pressure sensor may advantageously be arranged with its pressure-measuring surface in one of those surfaces in which the first conductor loop structure runs, and the second capacitive pressure sensor may advantageously be arranged with its pressure-measuring surface in one of those surfaces in which the second conductor loop structure runs.

Preferably, the first conductor loop structure and/or the second conductor loop structure may each be formed of a single wire. The latter may be bent to form all the turns of the conductor loop structure in question. Advantageously, turns of the first and of the second conductor structure which are located next to one another in the direction of the circumference around the main axis may also be connected to one another in some other way than by intermeshing. By way of example, these turns may be adhesively bonded to one another. However, an embodiment with intermeshing conductor structures is particularly advantageous because in this case no further production steps are necessary for the connection, and therefore the ease of production is increased.

Advantageously, the first resonant frequency may be greater than or equal to 5 MHz, preferably greater than or equal to 10 MHz, particularly preferably greater than or equal to 15 MHz and/or less than or equal to 40 MHz, preferably less than or equal to 30 MHz, particularly preferably less than or equal to 20 MHz.

Also provided according to the invention is a pressure wave measuring device which comprises on the one hand a passive transponder system, as described above, and additionally a reader unit. The reader unit has at least one reader coil, which can be arranged relative to the passive transponder system in such a way that a magnetic field generated by said reader coil passes through at least one of the conductor loop structures of the transponder system. The pressure wave measuring device according to the invention additionally comprises evaluation electronics, by means of which a signal that excites the resonant circuits of the passive transponder system can be applied to the reader coil. Here, the signal will be understood to be an alternating electromagnetic field which can pass through the conductor loop structures of the passive transponder system when it is arranged at a suitable distance from and at a suitable orientation to the passive transponder system. According to the invention, a signal received from the reader coil can also be evaluated by the evaluation electronics. The signal received from the reader coil is a curve of current over time, which is generated as a result of the reader coil being passed through by an electromagnetic field that is generated by the resonant circuits of the passive transponder system.

In one advantageous embodiment of the invention, the pressure wave measuring device may have a signal source, by means of which a signal, that is to say an alternating current curve, can be generated with the resonant frequencies of the resonant circuits. Advantageously, the pressure wave measuring device additionally has a directional coupler, to the output of which the signal source is electrically coupled and to the input of which the reader coil is coupled.

Advantageously, the signal may have the form a sin $(\omega_a t)$+b sin $(\omega_b t)$.

In a further advantageous embodiment of the invention, the pressure wave measuring device may have a first mixer, into which a signal received from the reader coil can be introduced. Downstream of the first mixer, there may be a low-pass filter, into which a signal output from the mixer can be introduced. A signal with the first resonant frequency that is received by the reader coil from the transponder system can be downmixed by means of the first mixer. The pressure wave measuring device of the invention may also have a further second mixer, into which a signal received from the reader coil can be introduced. Downstream of this further mixer, there may be a second low-pass filter, into which a signal output from the second mixer can be introduced. A signal with the second resonant frequency that is received by the reader coil from the transponder system can in turn be downmixed by means of the second mixer.

The pressure wave measuring device is preferably designed in such a way that the signal received with the first resonant frequency can be constructively added to the signal received with the second resonant frequency. If a mixer and a low-pass filter are provided as described above, advantageously the signal output from the first low-pass filter can be constructively added to the signal output from the second low-pass filter. This constructive addition may take place in that, on the one hand, the signal output from the first low-pass filter is split into absolute value or amplitude and phase, and additionally the signal output from the second low-pass filter is split into amplitude or absolute value and phase. Then, the absolute values or amplitudes can be added to one another and the phases can be added to one another, resulting in a sum amplitude and a sum phase.

The measurement principle may correspond to a lock-in amplifier. The first resonant circuit and the second resonant circuit deliver an X component and a Y component, which are received by the reader coil. If $\omega_a$ and $\omega_b$ are the resonant frequencies of the two resonant circuits of the passive transponder system at a given trigger pressure $p_t$, then the signal can be predefined as described above and can be coupled into the coils of the passive transponder system. Resonant frequencies may lie for example in a range from 1 to 100 MHz, it being possible for the frequency components of the applied pressure to lie for example between 0.1 and 50 Hz. For use on a blood vessel, the main component may be for example a heartbeat that repeats periodically at around 1 Hz.

The signal source may then emit a signal with the two frequencies of interest $\omega_a$ and $\omega_b$ and transmit said signal to the output of the directional coupler. The directional coupler can transmit the signal at its input and forward it to the reader coil. Due to the directional coupler, direct transmission of the signal from the signal source to the mixer does not take place (or only to a very limited extent for real directional couplers, with an insulation parameter of greater than 25 dB). However, usually signals which are reflected by the coil due to the deviation from the system impedance (for example 50 Ohm) are able to pass from the reader coil to the mixers.

If the sensors of the passive transponder system then change their resonant frequencies $\omega_a$ and $\omega_b$ as a result of changes in the pressure applied to the capacitive pressure sensors, this can be measured in the reflected signal since a change is brought about in the impedance of the reader coil and thus in the reflected signal.

Downmixing of the signal and filtering using a low-pass filter with the resonant frequencies $\omega_a$ and $\omega_b$ to be observed is advantageous since, for a large measurement bandwidth, the noise level can also usually assume large values and then the change in the reflected signal may be relatively weak in the case of sensors located far away and for example in the body tissue. The information thus obtained then thus exists directly in the baseband. Separating the two signals into amplitude and phase is advantageous since said signals can thus be added without cancelling one another out at certain angles.

The mixer may advantageously multiply the measured signal by the reference signal, which is generated by the signal source, and thus bring about a frequency shift in the spectrum of the measured signal by the reference frequency. The frequency component at the reference frequency which is contained in the measured signal can thus be downmixed to zero. The subsequent low-pass filtering can advantageously remove further mixing products and reduce the noise.

According to the invention, a method for producing a passive transponder as described above is also specified. The first and/or the second conductor loop structure are produced as follows. First, a plurality of carrier elements are strung onto a rod. Each of these carrier elements has a cylindrical outer surface, in which a cutout is formed. This cutout has a surface area which is in turn part of a cylindrical surface. Advantageously, this cylindrical surface has the same curvature as the outer surface of the carrier element. In addition, the cylinder axis of this cylindrical surface of the cutout is advantageously perpendicular to the cylinder axis of the outer surface of the carrier element. In this way, a plurality of carrier elements can be strung onto the rod, wherein in each case the cylinder axes of the cylindrical outer surface of adjacent carrier elements are perpendicular to one another.

A first wire is then wound as a first conductor loop structure around a first group of carrier elements. The first group of carrier elements is characterized in that the cylinder axes of their outer surfaces are all parallel to one another.

In addition, a second wire is wound as a second conductor loop structure around a second group of carrier elements, wherein this second group in turn contains those carrier elements whose cylinder axes are parallel to one another but perpendicular to the cylinder axes of the carrier elements of the first group. In this way, the first and the second conductor loop structure can be wound with turn axes which are perpendicular to one another.

On completion of winding, the rod can be pulled out from all the carrier elements so that the latter are freely movable and can be pushed out of the windings. Therefore, only the wound conductor loop structures remain. Advantageously, the first and the second wire can each be wound in such a way that they firstly run fully around a carrier element of the relevant group at least once and then run onwards to the respectively adjacent carrier element of the same group. They can in turn run fully around the latter and then run onwards to the subsequent further carrier element of the same group. In this way, conductor loop structures can be produced with a plurality of turns arranged next to one another. By using the carrier elements, it becomes possible in particular to wind in such a way that the first and the second windings respectively run in two opposite surfaces. In addition, it is readily possible to pass the wire of the first conductor loop structure through the turns of the second conductor loop structure and to pass the wire of the second conductor loop structure through the turns of the first conductor loop structure, so that a stable woven structure is obtained. It should be noted that the cylinder axis of the outer surfaces of the carrier elements may correspond to the turn axes of the turn wound around said carrier element, and that the longitudinal axis of the rod corresponds to the main axis of the passive transponder system.

The invention will be explained below by way of example and with reference to some figures. Identical reference signs correspond to identical or corresponding features. The features shown in the examples may also be implemented independently of the example in question and may be combined between the examples.

Figure 1:
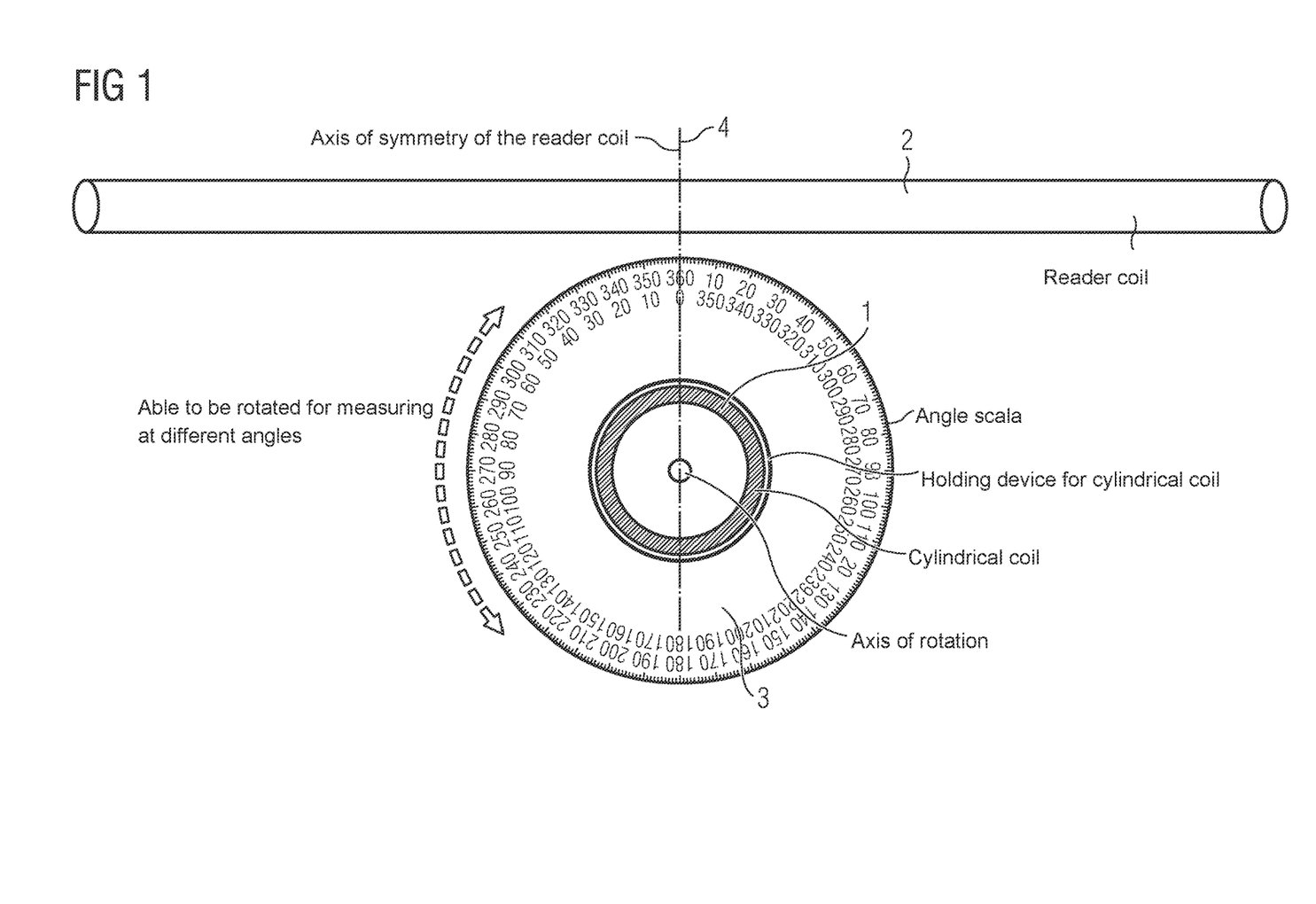
FIG. 1 shows a measuring arrangement for determining a directional characteristic of a transponder.

FIG. 1 shows a measuring arrangement for measuring the directional characteristic of a transponder 1. The transponder 1 is arranged here with a variable orientation relative to a reader coil 2. The measuring device has an optional angle scale 3, by which the orientation of the transponder can be measured. Here, the reader coil 2 is a cylindrical coil, which can be seen from the side in FIG. 1. The transponder 1 is arranged relative to the reader coil 2 in such a way that an axis of symmetry 4 of the reader coil 2 intersects a cylinder axis of the transponder 1, the axis of symmetry 4 being perpendicular both to the reader coil 2 and to the cylinder axis of the transponder 1. Here, the transponder 1 has saddle-shaped coils which are arranged on cylindrical surfaces of the transponder 1, namely in such a way that the coil axes are perpendicular to the longitudinal axis of the transponder 1 and intersect the axis of symmetry 4 or are coaxial to the latter. The coil axes additionally intersect the cylinder axis of the transponder 1, here the axis of rotation.

Figure 2:
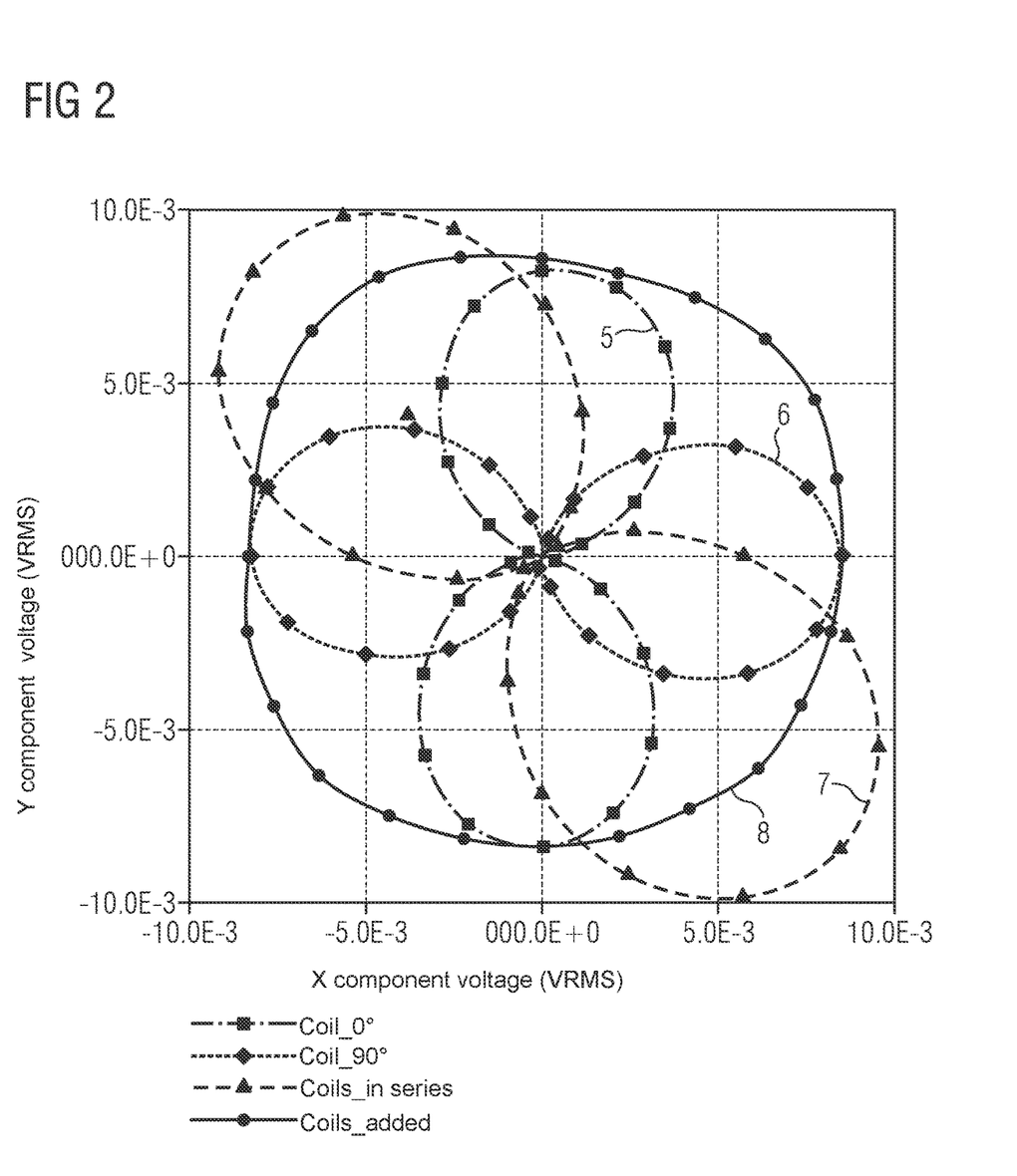
FIG. 2 shows a directional characteristic of a transponder comprising two coils.

FIG. 2 shows a directional characteristic as measured for a transponder by means of the measuring arrangement shown in FIG. 1 when the transponder 2 has cylindrical coils, the coil axes of which are perpendicular to one another and intersect one another. FIG. 2 shows the X component of the voltage induced in the reader coil and the Y component of the voltage induced in the reader coil, wherein the coil axis of one coil of the transponder runs in the X direction and the coil axis of the other coil of the transponder runs in the Y direction.

The dotted line 5 (squares) in FIG. 2 shows the directional characteristic of that coil of the transponder which has a coil axis oriented in the Y direction. The line 6 shown in small dashes (spots) shows the directional characteristic of that coil of the transponder which has a coil axis oriented in the X direction. It can be seen that the two individual coils of the transponder 1 have a pronounced figure-of-eight-shaped directional characteristic, the directional characteristics of the two coils being rotated through 90° relative to one another since the coils are also rotated through 90° relative to one another. If the two coils of the transponder 1 are simply connected in series, then the directional characteristic 7 shown in large dashes (triangles) is obtained, which is likewise figure-of-eight-shaped and is rotated through 45° relative to the directional characteristics of the two individual coils. The solid line (circles) shows the directional characteristic of a transponder according to the present invention. Since the signals of the two individual coils differ from one another due to their different resonant frequencies, the signals of the two coils can be constructively added to one another. This results in the directional characteristic denoted 8, which is almost circular. The direction in which reading takes place in the XY plane is of no importance here. A good coupling between the transponder and the reader coil is always achieved.

Figure 3:
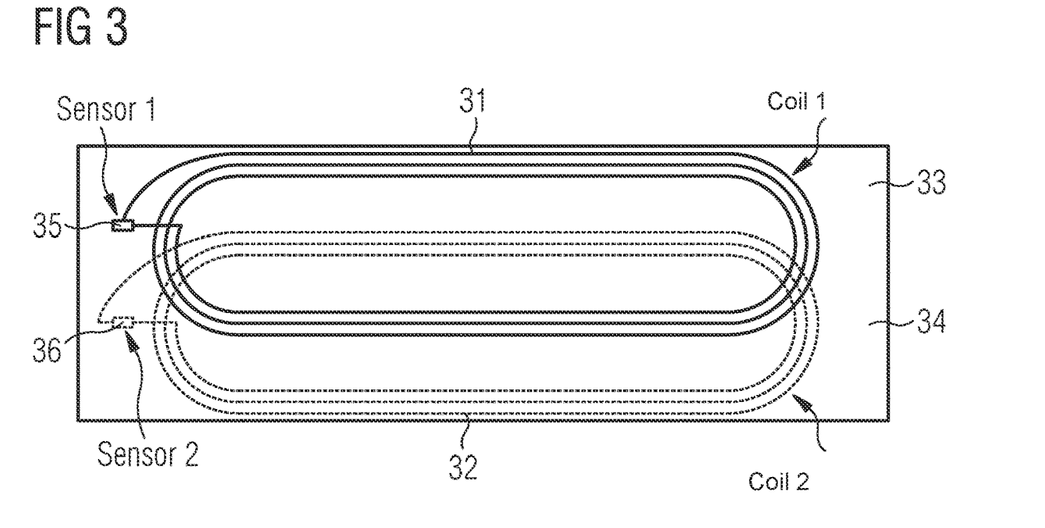
FIG. 3 shows a printed circuit for producing an exemplary transponder system according to the invention.
Figure 4A:
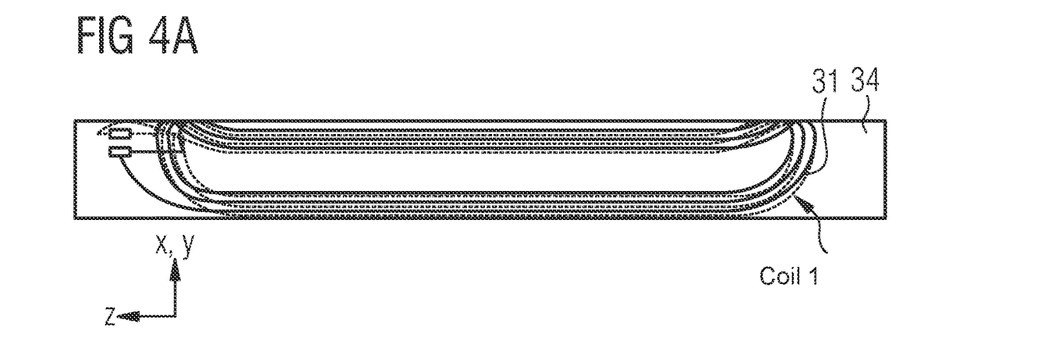
FIG. 4 shows a side view of this transponder system according to the invention.
Figure 5:
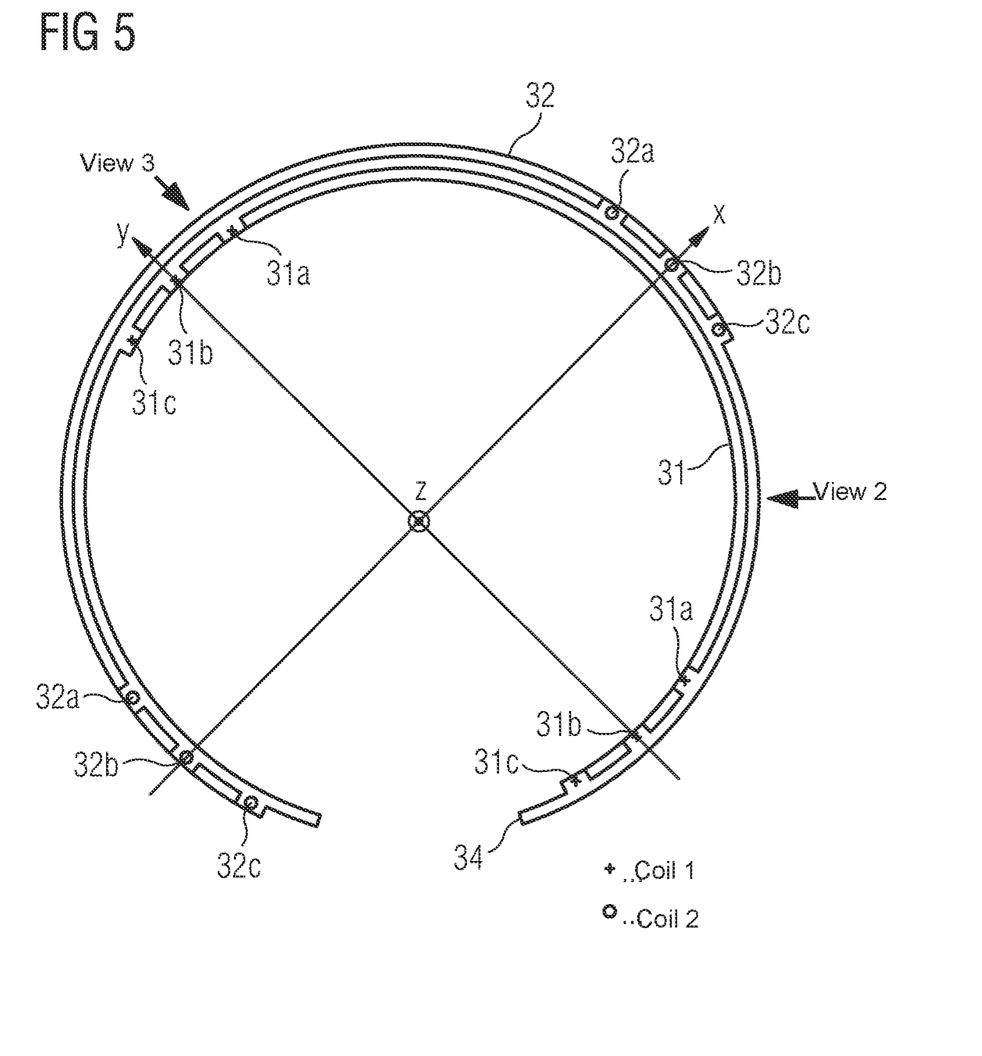
FIG. 5 shows an axial view of this transponder system according to the invention.

FIGS. 3 to 5 show a first example of a passive transponder according to the invention. FIG. 3 shows a printed circuit, from which the transponder can be produced, FIG. 4 shows two side views of the transponder thus produced, and FIG. 5 shows an axial view of the transponder thus produced.

FIG. 3 shows a printed circuit 33 comprising a first conductor loop structure 31 and a second conductor loop structure. The conductor loop structure 31 is applied to a front side of a substrate 34, facing towards the observer in FIG. 3, and the second conductor loop structure is applied to a rear side of the substrate 34, facing away from the observer. The substrate 34 thus electrically insulates the first conductor loop structure 31 and the second conductor loop structure 32 from one another.

In the example shown, the conductor loop structures 31 and 32 each have three turns. Each of the conductor loop structures 31 and 32 has two straight regions, which are parallel to one another and are connected to one another via two circularly curved regions. In the straight regions the conductor tracks run parallel to one another and in a straight line, and in the circularly curved regions the conductor tracks run along a circular line and parallel to one another for all turns of the same conductor loop structure. A first capacitive pressure sensor 35 is coupled to the first conductor loop structure 31. The capacitive pressure sensor 35 is coupled between the two ends of the conductor loop structure 31. Correspondingly, the conductor loop structure 32 has a second capacitive pressure sensor 36, which is once again arranged between the two ends of the conductor loop structure 32. The first capacitive pressure sensor 35 together with the first conductor loop structure 31 forms a first resonant circuit with a first resonant frequency. The second capacitive pressure sensor 36 together with the second conductor loop structure 32 forms a second resonant circuit with a second resonant frequency.

The first conductor loop structure 31 is wound around a turn axis, the turn axis here passing through the centre point of the conductor tracks of the conductor loop structure 31 and being perpendicular to the substrate 34. Correspondingly, the conductor tracks of the second conductor loop structure 32 are wound around a second coil axis, which once again runs through the centre point of the conductor tracks of the second conductor loop structure 32 and is perpendicular to the substrate 34.

From the structure shown in FIG. 3, it is possible to produce a passive transponder according to the invention as shown in FIG. 4 by bending the substrate 34 about an axis which runs parallel to the longitudinal sides of the substrate 34, which are parallel to the straight sections of the conductor loop structures 31 and 32. This direction will be referred to below as the Z direction.

FIG. 4A shows this embodiment of the transponder in a first direction which is perpendicular to the Z direction and at an angle of 45° to the X axis and to the Y axis. Sub-FIG. 4B shows the transponder as seen in the direction of the X axis.

The conductor loop structures 31 and 32 may advantageously be dimensioned such that, when the substrate 34 is bent in the described manner, the straight regions of the conductor loop structures are located precisely diametrically opposite one another in relation to the axis about which the substrate 34 has been bent. The substrate 34 is preferably bent in a circular shape so that the coil axes of the first conductor loop structure and of the second conductor loop structure 32 are at the desired angle to one another, preferably perpendicular to one another.

FIG. 5 shows the embodiment of the transponder according to the invention which is shown in FIG. 4, as viewed in the direction of the Z axis. The view shown in FIG. 4A is obtained when looking at the view shown in FIG. 5 from the right, and the view shown in FIG. 4B is obtained when looking at it from the top left-hand corner.

It can be seen that the substrate has been bent into a circular shape. The first conductor loop structure 31 is located on an inner surface of the resulting cylindrical substrate, and the second conductor loop structure 32 is located on the outer surface thereof. The longitudinal regions 31a, 31b and 31c of the first conductor loop structure 31 are located one another, in relation to which the straight sections 31a, 31b, 31c of the same turn of the first conductor loop structure 31 are at the same distance. Correspondingly, the straight sections 32a, 32b, 32c are located opposite one another in relation to the YZ plane, the straight sections 32a, 32b, 32c of the same turn being at the same distance therefrom.

Figure 6:
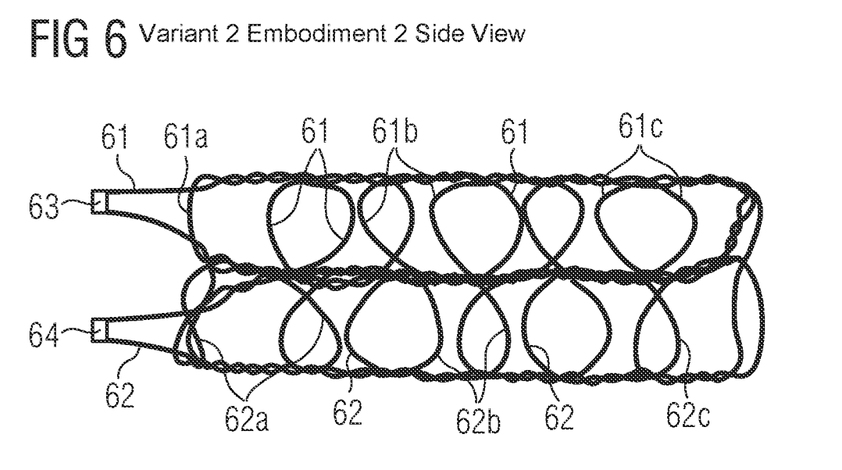
FIG. 6 shows a further example of a transponder system according to the invention.
Figure 7:
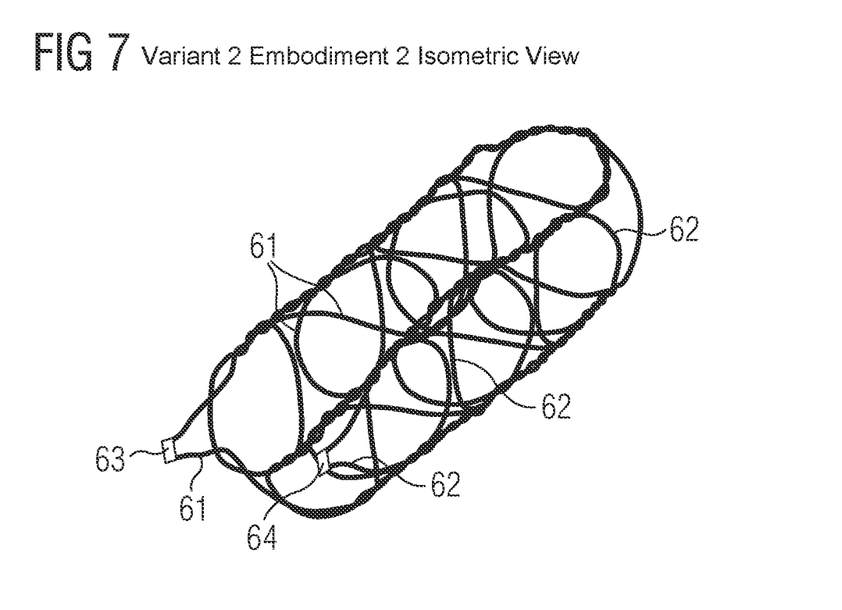
FIG. 7 shows a perspective view of the transponder system shown in FIG. 6.
Figure 8:
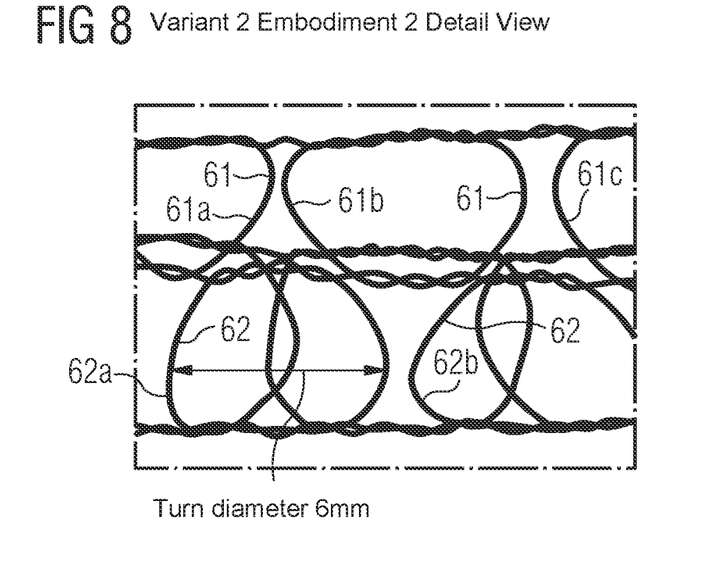
FIG. 8 shows a detail view of the transponder system shown in FIGS. 6 and 7.
Figure 9:
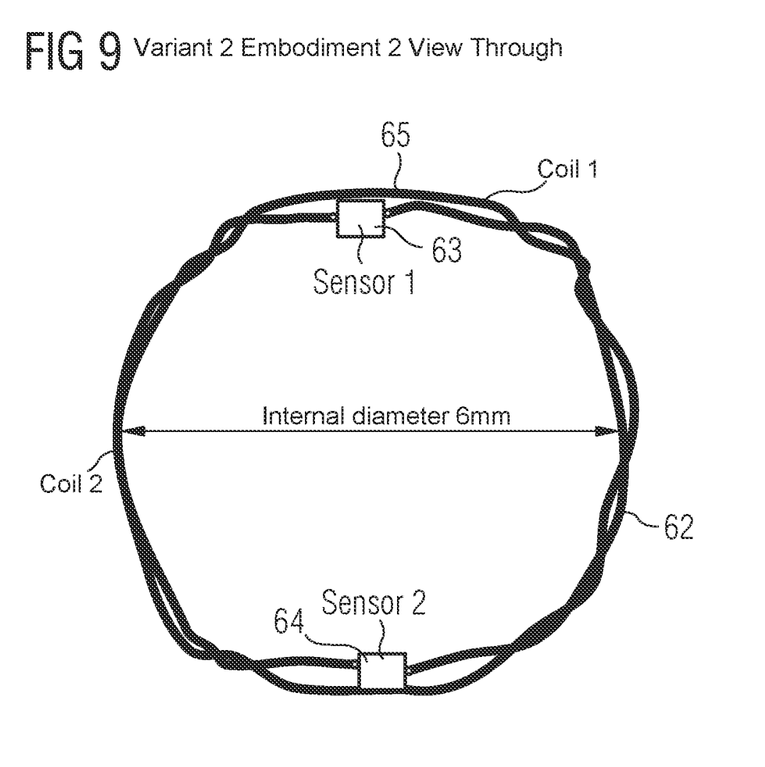
FIG. 9 shows an axial view of the transponder system according to the invention shown in FIGS. 6 to 8.

FIGS. 6 to 9 show a further example of a passive transponder according to the invention. FIG. 6 shows a side view in the direction perpendicular to the Z axis, which corresponds to the longitudinal axis or main axis of the transponder, FIG. 7 shows a perspective view, and FIG. 8 shows a detail view. FIG. 9 shows a view in the direction of the Z axis.

In this embodiment of the invention, a first wire 61 is bent to form a first conductor loop structure 61 and a second wire 62 is bent to form a second conductor loop structure 62. The first conductor loop structure 61 has a plurality of turns 61a, 61b, 61c arranged next to one another in the direction of a main axis, which here is the longitudinal axis, that is to say the Z direction of the transponder, each of the turns of the first conductor loop structure 61 being wound around a separate turn axis. The first turn axes are parallel to one another and are spaced apart from one another by a non-vanishing distance. The illustrated embodiment additionally has a second conductor loop structure 62 with a plurality of turns 62a, 62b, 62c arranged next to one another in a direction of the main axis, each of the turns 62a, 62b, 62c of the second conductor loop structure 62 once again being wound around a separate second turn axis. The second turn axes are once again parallel to one another and are spaced apart from one another by a non-vanishing distance. In the illustrated example, the turn axes of the first turns 61a, 61b, 61c are additionally perpendicular to the turn axes of the second turns 62a, 62b, 62c. In the illustrated example, the conductor loop structure 61 additionally has, on each of the turn axes, two turns which are located opposite one another in relation to the Z axis. In addition, the second conductor loop structure 62 also has, for each of the turn axes, two turns located opposite one another in relation to the Z axis.

As can be seen in the detail in FIG. 8, the turns 61a, 61b, 61c of the first conductor loop structure 61 are interwoven with the turns 62a, 62b of the second conductor loop structure 62. To this end, the wire of the first conductor loop structure 61 is firstly bent to form a substantially circular turn, the turn being closed as a result of the wire being wound around the wire of the second conductor loop structure 62, where it runs between two turns 62a and 62b of the second conductor loop structure. Correspondingly, the wire of the second conductor loop structure 62 is bent to form a turn 62a which is closed as a result of the wire being wound around the wire of the first conductor loop structure 61, where it runs between two adjacent turns 61a and 61b of the first conductor loop structure. In this way, for each of the conductor loop structures 61 and 62, in each case the wire is bent to form a turn, then is guided along a straight region parallel to the cylinder axis of the transponder to the adjacent turn of the same conductor loop structure, is bent there once again into a turn and is guided onwards in a straight region to the adjacent turn of the same conductor loop structure, this being repeated for the number of turns in the same surface of the relevant conductor loop structure. The second conductor loop structure is correspondingly wound to form turns 62a, 62b, which are once again guided over straight regions parallel to the longitudinal axis of the transponder. The turns of the second conductor loop structure 62 are in each case wound in a sub-region of the turns around the straight region of the first conductor loop structure 61. Correspondingly, the turns 61a, 61b, 61c of the first conductor loop structure 61 are wound in the region of the turn around the straight region of the adjacent second conductor loop structure.

It should be pointed out that the form of winding shown here is merely one advantageous example that results in good mechanical stability. However, many other types of winding are conceivable which lead to an identical arrangement of the turns of the conductor loop structures 61 and 62. It is also possible that the conductors of the conductor loop structures 61 and 62 are connected to one another in some other way, for example by adhesive bonding or by being bound together.

FIG. 9 shows a view of the example of the transponder according to the invention shown in FIGS. 6 to 8, as seen in the direction of the longitudinal axis of the transponder, that is to say in the direction of the Z axis. It can be seen that the conductor loop structures 61 and 62 describe an approximately circular circumference, so that the transponder as a whole describes approximately a cylinder shape.

Here, too, the first conductor loop structure 62 is coupled at its ends to a first capacitive pressure sensor 63, and the second conductor loop structure 62 is coupled to a second capacitive pressure sensor 64.

Figure 10:
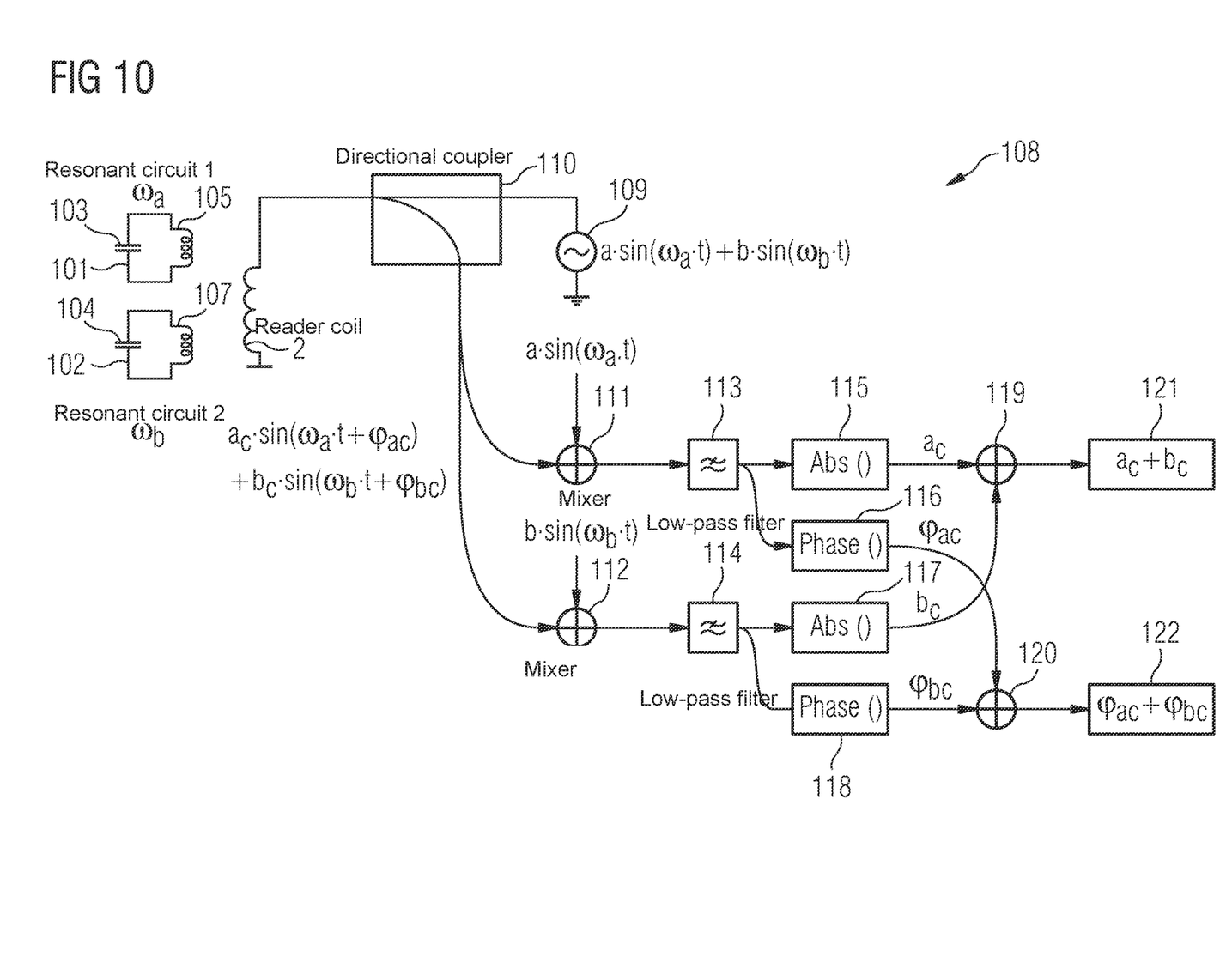
FIG. 10 shows an example of a pressure wave measuring device according to the invention.

FIG. 10 shows an exemplary circuit diagram of an inventive pressure wave measuring device according to the invention. The pressure wave measuring device according to the invention comprises a passive transponder as described above, which is illustrated here by a first resonant circuit 101 and a second resonant circuit 102. The first resonant circuit 101 has a first capacitive pressure sensor 103 and the second resonant circuit 2 has a second capacitive pressure sensor 104, which are shown as capacitances in FIG. 10. In addition, the first resonant circuit 101 has a first conductor loop structure 105 and the second resonant circuit has a second conductor loop structure 107.

The measuring device shown in FIG. 10 additionally comprises a reader unit 108, by means of which the resonant circuits 101 and 102 can be read. The reader unit 108 has a reader coil 2. By means of a signal source 109, it is possible to generate a signal, that is to say a current signal, with two superposed frequencies $\omega_a$ and $\omega_b$, wherein the component with the frequency $\omega_a$ is generated with an amplitude a and the component with the frequency $\omega_b$ is generated with an amplitude b. The signal form a·sin($\omega_a$t)+b·sin(wbt) is thus obtained. The signal thus generated is fed via a directional coupler 110 into the reader coil 2. The directional coupler is coupled to a first mixer 111 and to a second mixer 112, into which a signal received by the directional coupler 110 from the reader coil 2 can be fed. The signal obtained from the reader coil is mixed with the reference signal a·sin($\omega_a$t) in the first mixer 111 and with the reference signal b·sin($\omega_b$t) in the second mixer 112.

The signal output from the first mixer 111 is then fed to a low-pass filter 113. The signal output from the second mixer 112 is fed to a low-pass filter 114. The first low-pass filter 113 is then split by the reader unit 108 into an absolute value or an amplitude 115 and a phase 116. The signal output from the second low-pass filter 114 is likewise split into an amplitude 117 and a phase 118. The absolute values 115 and 117 of the first and second signal are added by means of an addition 119 in order to obtain a sum 121. The phases 116 and 118 of the first and second signal are added by means of a further adder 120 in order to obtain a sum 122. The signal 121 and 122 thus obtained then has a circular directional characteristic, as shown by the solid line (circles) in FIG. 2.

It should be pointed out that the mixers 111, 112 and the low-pass filters 113, 114 serve to improve the signal. They are therefore optional.

Figures 11, 12:
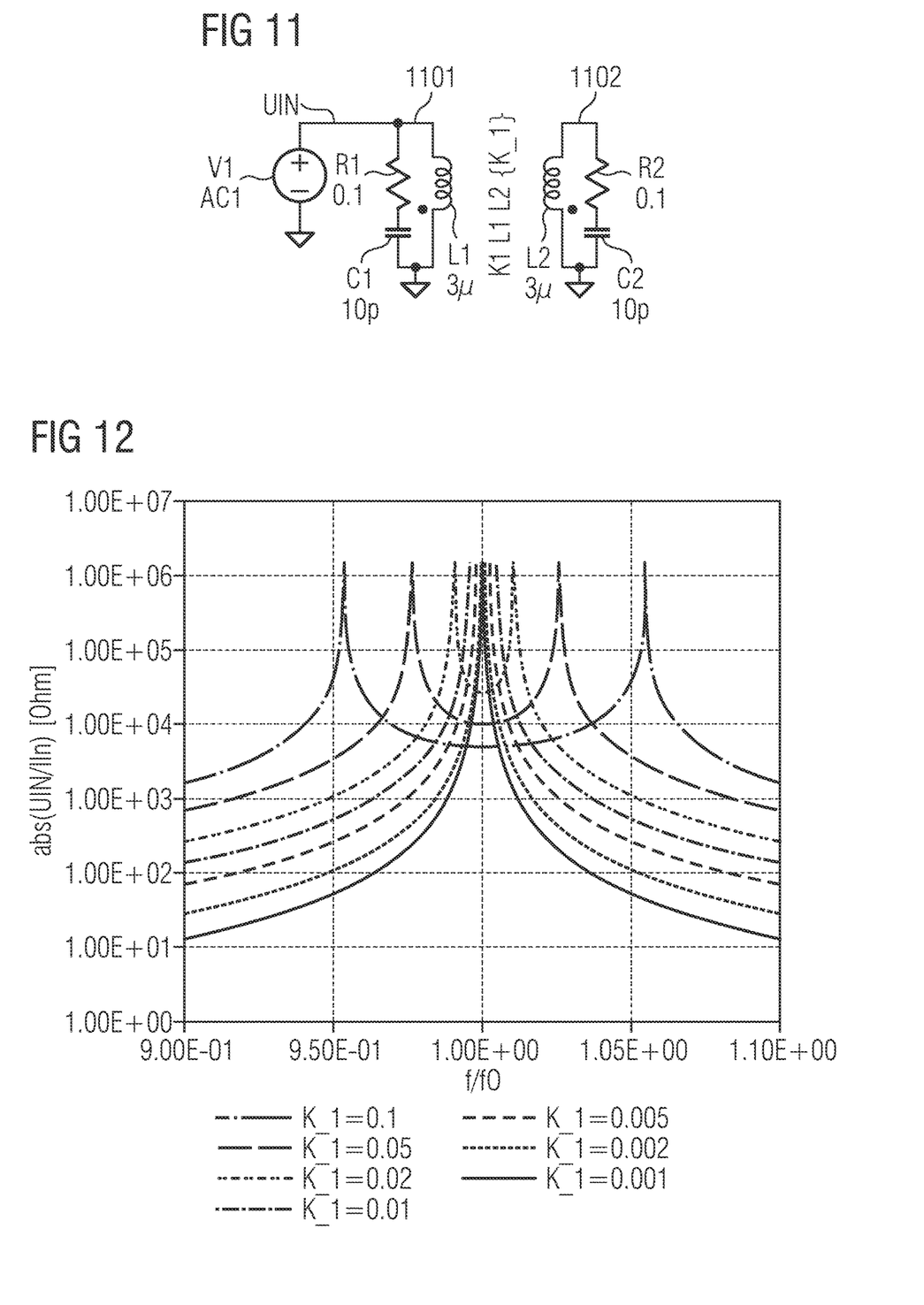
FIG. 11 shows an exemplary connection of two resonant circuits tuned to the same frequency.
FIG. 12 shows the resonance shift of the resonant circuits shown in FIG. 11.

FIG. 11 shows a circuit in which two resonant circuits 1101 and 1102 set to the same frequency are coupled to one another via two coils L1 and L2 with a coupling factor K1. The interaction thereof is illustrated as a function of K1. The greater K1, the greater the interaction between the coils C1 and C2 and the greater a resulting detuning. Besides the coil L1, which in the illustrated example has an inductance of 3μ, the first resonant circuit has a capacitance C1 of 10 pF and a resistance R1 having a value of 0.1Ω. The second resonant circuit 1102 comprises the second coil C2, a second capacitance C2 and a second resistance R2 having the same values as in the first resonant circuit 1101, so that the two resonant circuits 1101 and 1102 have the same resonant frequency. A voltage V1 is applied to the first resonant circuit 1101, by means of which the latter can be made to oscillate.

FIG. 12 shows the impedance UIN/IIn, measured in the first resonant circuit, as a function of the frequency $f/f_0$ for different coupling factors K1. The value $f_0$ is the resonant frequency of the two resonant circuits 1101 and 1102 in the uncoupled state. The various curves show different values of the coupling factor K1. It can be seen that there is no shift in the resonant frequency with a very small coupling of K1=0.001 (solid line). If the coupling is increased, however, it can be seen that the resonant frequencies of the two resonant circuits diverge.

FIG. 13 shows an exemplary production method for producing a passive transponder according to the invention. In a first step, a plurality of carrier elements 132 are strung onto a rod 131. Each carrier element 132 has a cylindrical outer surface, in which a cutout 133 shaped as part of a cylindrical surface is formed. The carrier elements 132 are strung onto the rod in such a way that the cylinder axes of their cylindrical outer surfaces are perpendicular to a longitudinal direction of the rod 131, and in such a way that additionally in each case one of the carrier elements 132 is located in the cutout 133 shaped as part of a cylindrical surface of an adjacent carrier element 132. This state can be seen in FIG. 13B.

Figure 13A:
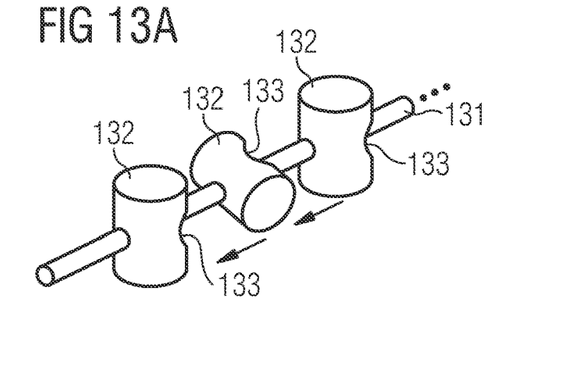
FIG. 13 shows an example of a production method according to the invention.
Figure 13B:
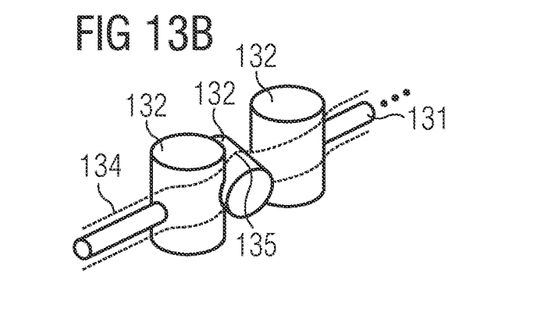
Figure 13C:
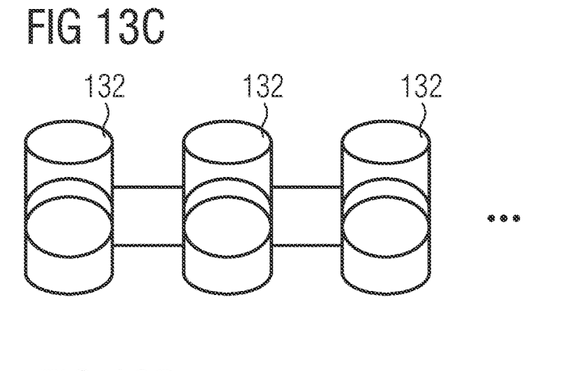
Figure 13D:
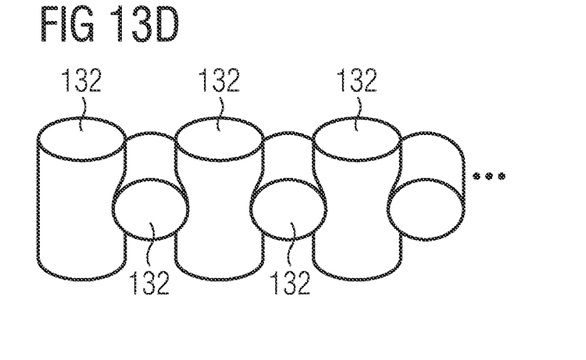

Carrier structures can also be produced as shown in FIGS. 13C and 13D, wherein the variant produced in 13D can be obtained from the method shown in sub-figures A and B.

Then, as illustrated in dotted line in FIG. 3B, a first wire as the first conductor loop structure and a second wire 135 as the second conductor loop structure 135 are wound around the carrier elements 132. The winding may take place in such a way as to result, for example, in a structure as shown in FIGS. 6 to 9. On completion of winding, the elements 132 can be removed so that only the conductor loop structures remain. To this end, the rod 131 shown in FIGS. 13A and 13B for example can be removed. Preferably, the wires 134 and 135 are each wound around each of the carrier elements 132 at least once, so that one turn is obtained in each case.

The invention claimed is:

1. A pressure wave measuring device comprising a passive transponder system and a reader unit,
   wherein the passive transponder system comprises
   a first conductor loop structure having at least one turn,
   a second conductor loop structure having at least one turn,
   a first capacitive pressure sensor,
   a second capacitive pressure sensor,
   wherein the first capacitive pressure sensor is electrically coupled to the first conductor loop structure to form a first resonant circuit with a first resonant frequency,
   wherein the second capacitive pressure sensor is electrically coupled to the second conductor loop structure to form a second resonant circuit with a second resonant frequency,
   wherein the at least one turn of the first conductor loop structure is wound around at least one first turn axis,
   wherein the at least one turn of the second conductor loop structure is wound around at least one second turn axis, and
   wherein the at least one first turn axis and the at least one second turn axis are at a non-vanishing angle to one another,
   wherein the reader unit has a reader coil which can be arranged relative to the passive transponder system in such a way that a magnetic field generated by said reader coil passes through at least one of the conductor loop structures of the transponder system,
   the pressure wave measuring device further comprising evaluation electronics, by means of which a signal that excites the resonant circuits can be applied to the reader coil and a signal received from the reader coil can be evaluated,
   the pressure wave measuring device further comprising a first mixer and a first low-pass filter arranged behind the first mixer, wherein a signal with the first resonant frequency that is received by the reader coil from the transponder system can be downmixed by means of the first mixer, and further comprising
   a further mixer and a second low-pass filter arranged behind the further mixer, wherein a signal with the second resonant frequency that is received by the reader coil from the transponder system can be downmixed by means of the further mixer,
   wherein the pressure wave measuring device is designed to constructively add a signal output from the first low-pass filter to a signal output from the second low-pass filter, or
   wherein the pressure wave measuring device is configured to separate a signal generated by the first low-pass filter into amplitude and phase and to separate a signal output from the second low-pass filter into amplitude and phase, and is further designed to add the amplitude separated from the signal generated by the first low-pass filter to the amplitude separated from the signal generated by the second low-pass filter.

2. The pressure wave measuring device according to claim 1, comprising a signal source, by means of which a signal can be generated with the resonant frequencies of the resonant circuits, and further comprising a directional coupler, to the output of which the signal source is electrically coupled and to the input of which the reader coil is coupled.

3. The pressure wave measuring device according to claim 1, wherein the first conductor loop structure and the second conductor loop structure are designed as flat coils which are arranged on surfaces of a carrier structure.

4. The pressure wave measuring device according to claim 3, wherein the first resonant frequency and the second resonant frequency differ from one another at least to such an extent that they do not superpose one another in such a way as to produce a beat.

5. The pressure wave measuring device according to claim 3, wherein the carrier structure is shaped as part of a cylinder or as a cylinder or as part of a hose or as part of a tube or as a hose or as a tube.

6. The pressure wave measuring device according to claim 5, wherein the carrier structure has or is a plastic tube.

7. The pressure wave measuring device according to claim 5, wherein the first conductor loop structure is arranged on an inner surface of the carrier structure and the second conductor loop structure is arranged on an outer surface of the carrier structure.

8. The pressure wave measuring device according to claim 3, wherein the first conductor loop structure has a plurality of groups of turns, the groups arranged next to one another in the direction of a main axis, each group comprising at least one turn, wherein each of the turns of the same group of the first conductor loop structure is wound around a common first turn axis, wherein the first turn axes of the different groups are in each case spaced apart from one another by a non-vanishing distance, and wherein the second conductor loop structure has a plurality of groups of turns, the groups arranged next to one another in the direction of the main axis, each group comprising at least one turn, wherein each of the turns of the same group of the second conductor loop structure is wound around a common second turn axis, wherein the second turn axes of the different groups are spaced apart from one another by a non-vanishing distance.

9. The pressure wave measuring device according to claim 8, wherein the first turn axes and/or the second turn axes are parallel to one another.

10. The pressure wave measuring device according to claim 9, wherein the turns of the first conductor loop structure extend in two surfaces located opposite one another in relation to the main axis, on which surfaces the first turn axes are perpendicular, and wherein the turns of the second conductor loop structure extend in two surfaces located opposite one another in relation to the main axis, on which surfaces the second turn axes are perpendicular.

11. The pressure wave measuring device according to claim 10, wherein the first turn axes are located between the second turn axes in the direction along the main axis.

12. The pressure wave measuring device according to claim 10, wherein the first capacitive pressure sensor is arranged with its pressure-measuring surface in one of those surfaces in which the first conductor loop structure runs and the second capacitive pressure sensor is arranged with its pressure-measuring surface in one of those surfaces in which the second conductor loop structure runs.

13. The pressure wave measuring device according to claim 12, wherein the resonant frequency of the first and of the second resonant circuit differ by at least twice the bandwidth of that one of the first or second resonant circuit that has the greater bandwidth.

14. The pressure wave measuring device according to claim 1, wherein the first conductor loop structure is formed from a single wire and/or wherein the second conductor loop structure is formed from a single wire.

15. The pressure wave measuring device according to claim 1, wherein the first resonant frequency and/or the second resonant frequency is greater than or equal to 5 MHz, and less than or equal to 40 MHz.

16. The pressure wave measuring device according to claim 1, wherein the first and the second conductor loop structure form a vessel support for a blood vessel or a stent.

17. The pressure wave measuring device according to claim 1, wherein the first and/or the second conductor loop structure is made of DFT wire having a core comprising silver or gold and having a sheath comprising NiTi.

* * * * *